(12) United States Patent
Allmon

(10) Patent No.: US 6,406,459 B1
(45) Date of Patent: Jun. 18, 2002

(54) NEEDLE SAFETY DEVICE

(76) Inventor: Butch Allmon, 983 CR 3673, Paradise, TX (US) 76073

(*) Notice: Subject to any disclaimer, the term of this patent is extended or adjusted under 35 U.S.C. 154(b) by 0 days.

(21) Appl. No.: 09/472,353

(22) Filed: Dec. 21, 1999

(51) Int. Cl.$^7$ .................................................. A61M 5/32
(52) U.S. Cl. ........................................ 604/192; 604/263
(58) Field of Search .............................. 604/110, 162, 604/164.08, 192, 263

(56) References Cited

U.S. PATENT DOCUMENTS

| | | | |
|---|---|---|---|
| 5,053,017 A | * 10/1991 | Chamuel | 604/192 |
| 5,344,408 A | 9/1994 | Partika | |
| 5,549,570 A | * 8/1996 | Rogalsky | 604/198 |
| 6,117,108 A | * 9/2000 | Woehr et al. | 604/110 |
| 6,210,373 B1 | * 4/2001 | Allmon | 604/192 |
| 6,280,419 B1 | * 8/2001 | Vojtasek | 604/192 |
| 6,287,278 B1 | * 9/2001 | Woehr et al. | 604/110 |

FOREIGN PATENT DOCUMENTS

| | | | |
|---|---|---|---|
| EP | 0753317 A1 | 1/1997 | A61M/5/32 |
| WO | WO9908742 | 2/1999 | A61M/25/06 |

* cited by examiner

*Primary Examiner*—Sharon Kennedy
(74) *Attorney, Agent, or Firm*—Blakely, Sokoloff, Taylor & Zafman

(57) ABSTRACT

An apparatus and a method are disclosed for a needle safety device comprising a needle having a proximal and a distal end, a flexible member having a proximal and distal end, and a housing. The member has an aperture to receive the needle. The proximal and distal end of the flexible member contacts the housing at an approximate first point located near the proximal end of the housing and at a second point located near the distal end of the housing.

20 Claims, 6 Drawing Sheets

NEEDLE SAFETY DEVICE

FIELD OF THE INVENTION

This invention relates generally to medical devices and more particularly to a needle safety device for safely closing a needle up a catheter.

BACKGROUND

Intravascular devices such as catheter assemblies are generally used for passing fluids between a device such as a syringe or a drip to or from body lumens such as veins or arteries, or other internal target sites. Such an assembly usually includes a hub, a catheter tube, and a needle. An eyelet ring is typically inserted into the catheter. The catheter tube, together with the eyelet ring, is then inserted into an opening in the nose of the hub and is secured to the hub by press fitting the eyelet ring within the nose of the hub. This hub and tube assembly is then mounted over a sharp needle which is in turn attached to a plastic hub. The sharp tip of the needle is used for piercing a body lumen so that access may be gained into the body lumen by the needle and subsequently the catheter. Once the catheter and the needle are located within the body lumen, the needle is removed and discarded while the catheter tube remains in the body lumen. A syringe or a tube of a drip is then attached to the hub so that fluids may be passed through the hub and the catheter between the drip or the syringe and the body lumen. The hub is typically made of materials that provide sufficient rigidity to securely attach drip lines thereto and the catheter tube is usually made of material which is flexible and soft to minimize bodily injury.

To prevent the used sharpened distal tip of a needle from inadvertently piercing the skin of a healthcare worker, a cover may be used in conjunction with an inner shield to cover the needle. U.S. Pat. No. 5,344,408, issued to Partika (Partika) represents an example of a device used in the art. In Partika, levers and teeth secure the needle such that the needle does not extend outside of a housing. More particularly, one lever arm is configured with an aperture for receiving the needle and the distal end of the lever arm contacts the inner surface of the housing. However, this assembly is not stable since the lever arm contacts only one point of the assembly. The assembly may become detached if a force is applied to the proximal end of the lever arm. It is therefore desirable to have an assembly that increases the stability of the needle within a housing to prevent dislodgement of the assembly.

SUMMARY

An apparatus and a method are disclosed for a needle safety device comprising a needle having a proximal and a distal end, a flexible member having a proximal and distal end and an aperture to receive the needle, and a housing. The proximal and distal end of the flexible member contacts the housing at a first point located near the proximal end of the housing and at a second point located near the distal end of the housing. Additional features, embodiments, and benefits will be evident in view of the figures and detailed description presented herein.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION

A method and an apparatus for securing a needle safety device assembly is disclosed. In the following description, numerous specific details are set forth in order to provide a more thorough understanding of the present invention. It will be apparent, however, to one skilled in the art, that the present invention may be practiced without employing these specific details. In other instances, well known processes and processing techniques have not been described in detail in order to avoid unnecessarily obscuring the present invention.

Figure 1:
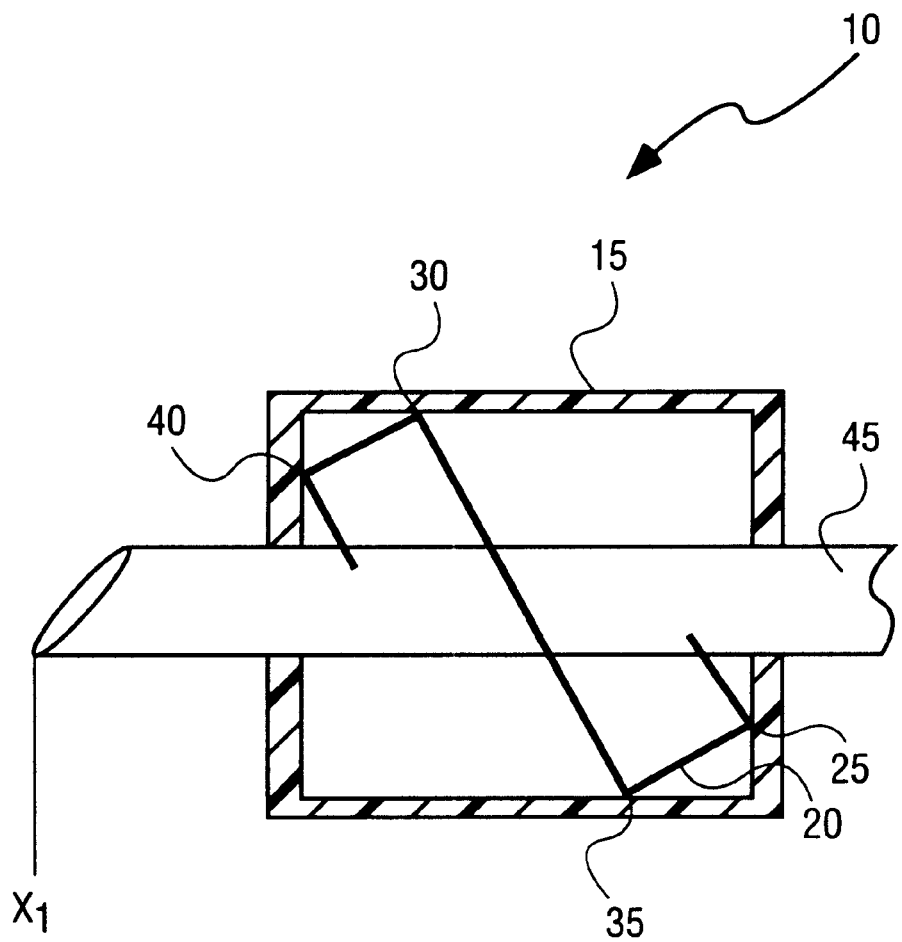
FIG. 1 is a cross-sectional view of an embodiment of the invention wherein a member is in an unlocked position.
Figure 2:
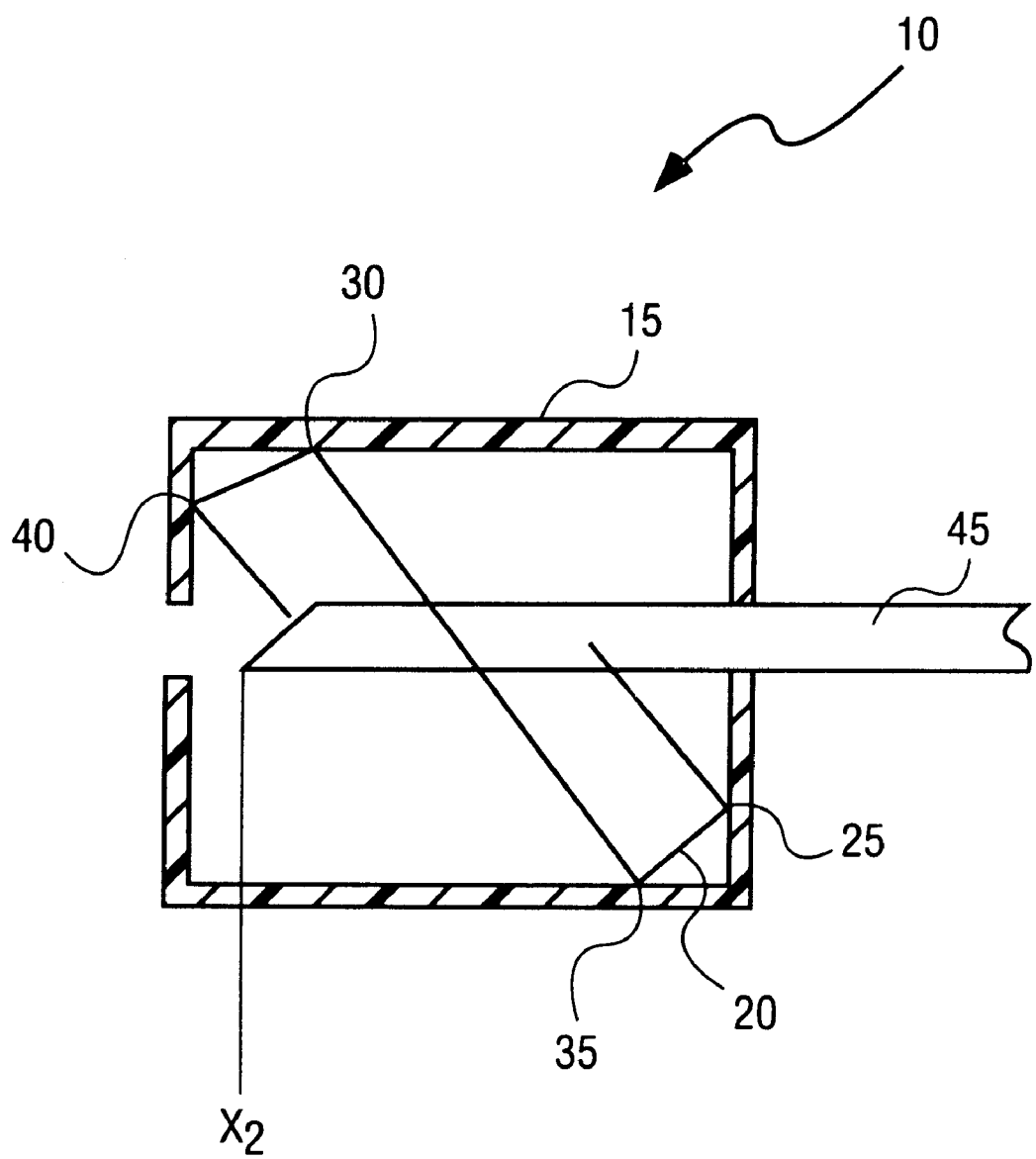
FIG. 2 is a cross-sectional view of an embodiment of the invention wherein the member is in a locked position.

FIGS. 1–4 show one embodiment of the invention. Assembly 10 includes housing 15, needle 45, and member 20. Housing 15 has a proximal end and a distal end. Additionally, housing 15 has opposing sides that are connected to the proximal and distal ends. Member 20 is comprised of a flexible material such as stainless steel shunt stock that allows member 20 to be bent by a variety of methods including using a die to press on member 20 to form an angle at various points in member 20. Member 20 has at least two points in which member 20 is angled. These angles may range from approximately 20° to 90°. The angled points in member 20 are represented by first contact point 30 and second contact point 40. It will be appreciated that by having first contact point 30 and second contact point 40 at different points of the inner surface of housing 15, one embodiment of the invention is able to provide greater stability for holding needle 45 securely in place prior to, during, and after the insertion of needle 45 into a patient. In addition to first and second contact points (30, 40), third contact point 25 and fourth contact point 35 between member 20 and housing 15 provide additional support for securely holding needle 45 in place. Thus, in this embodiment the member 20 has a substantially "Z-shaped" profile as shown in FIGS. 1 and 2.

Member 20 further has aperture 42 to receive needle 45. Although it is shown that aperture 42 is substantially centrally located in member 20, it will be appreciated that other configurations are also useful to practice the invention. For example, member 20 may have a plurality of angled points that allow member 20 to have more than one location to receive needle 45.

Figure 3:
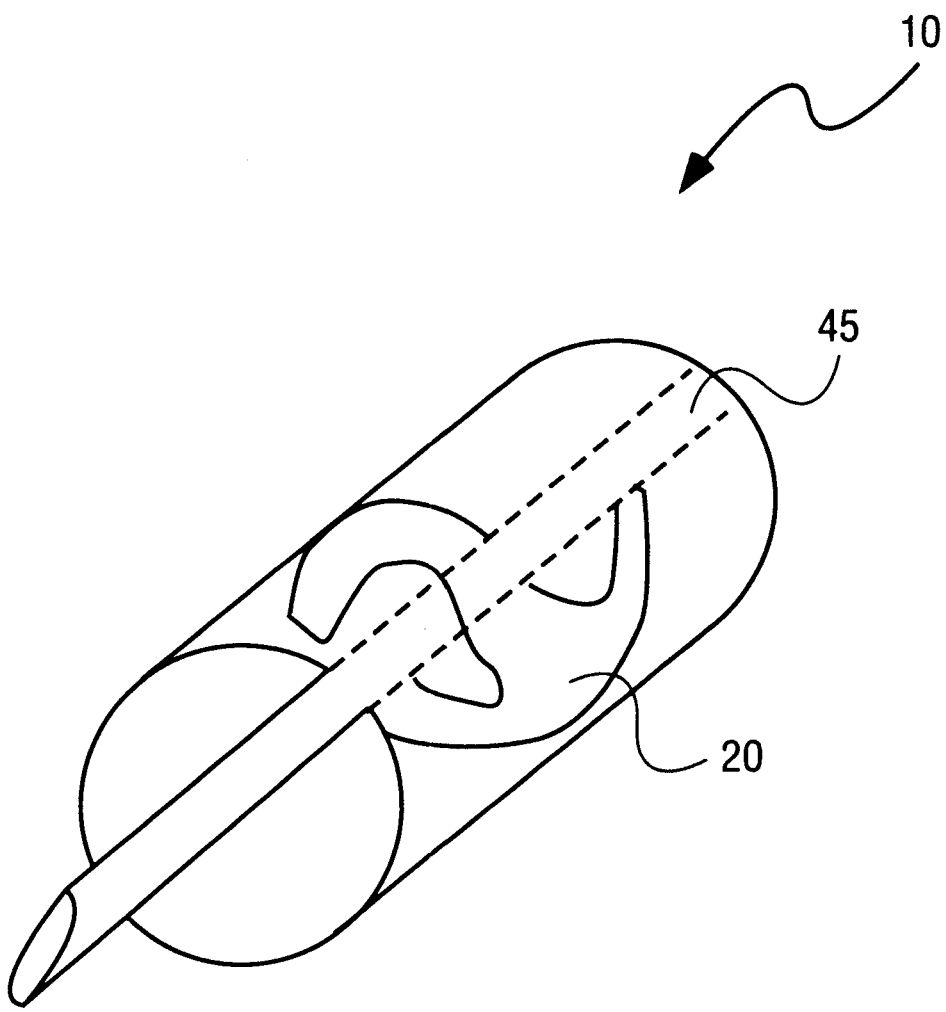
FIG. 3 is an isometric view of an embodiment of the invention wherein a member is in a locked position.

FIGS. 1 and 3 illustrate member 20 in an unlocked position in which needle 45 extends through housing 15 to $X_1$. Needle 45 is in the unlocked position during insertion of needle 45 into the patent and while needle 45 is in the patent. The distal and proximal end of member 20 lays against member 20. While the distal end of member 20 is adjacent to member 20, needle 45 is capable of moving within aperture 100 of member 20.

Figure 4:
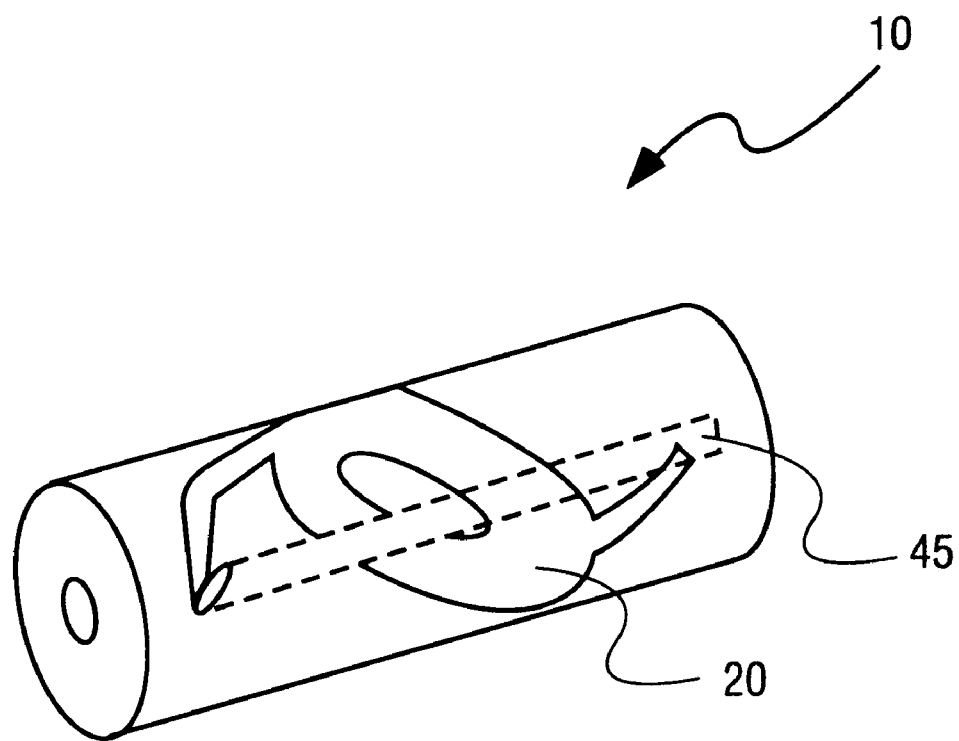
FIG. 4 is an isometric view of an embodiment of the invention wherein a member is in a locked position.

FIG. 2 illustrates a cross-sectional view and FIG. 4 shows an isometric view of the locked position at $X_2$ of member 20. Once needle 45 is removed from the patient and the catheter (not shown). The distal end of member 20 contacts the beveled end of needle 45 after needle 45 slides out of the catheter (not shown). When the distal end of member 20 contacts the beveled tip of needle 45, a clicking or snapping noise is produced. This noise indicates to the healthcare worker that needle 45 is securely in place within housing 15 and that the healthcare worker is safe from inadvertently piercing his or her skin by the used needle.

Figure 5:
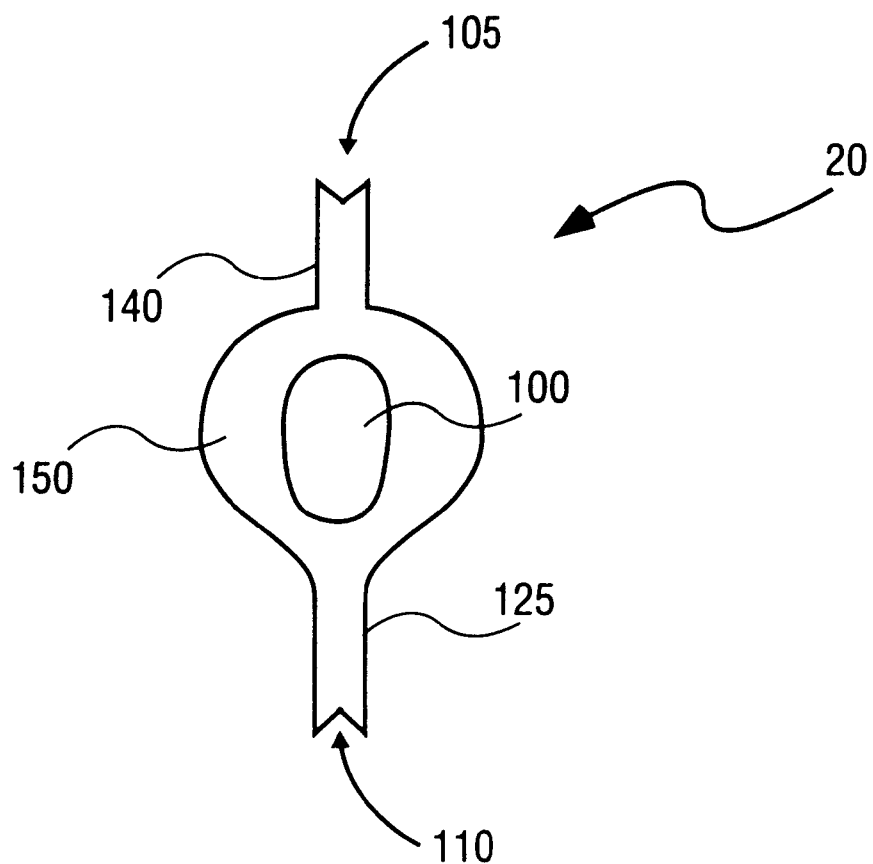
FIG. 5 is an enlarged sectional view of a member used in accordance with one embodiment of the present invention.

FIG. 5 shows an enlarged sectional view of a member used in accordance with one embodiment of the invention. FIG. 5 shows that wall 150 forms aperture 100. Although aperture 100 is shown to have a top portion that is substantially circular in shape and a lower portion that is substantially elliptical in shape, other shapes may also be used. For example, aperture 100 may be circular, rectangular, egg-shaped, or any other suitable shape for securely holding member 20. Needle 45 slides through the large portion of aperture 100 while needle 45 is in the unlocked position shown in FIGS. 1 and 3.

Protruding from wall 150 is first arm 140 and second arm 125. Extending at the distal end of first arm 140 is first recess region 105 and extending from second arm 125 is second recess region 110. These recessed regions may also be referred to as indentations and are used to contact the outer surface of needle 45 or alternatively, contact the inner surface of housing 15. Member 20 is generally greater in length than housing 15 to allow for tension to exist in member 20 when it is forced to conform to the inner dimensions of housing 15 which thereby increases the pressure against housing 15.

Figure 6:
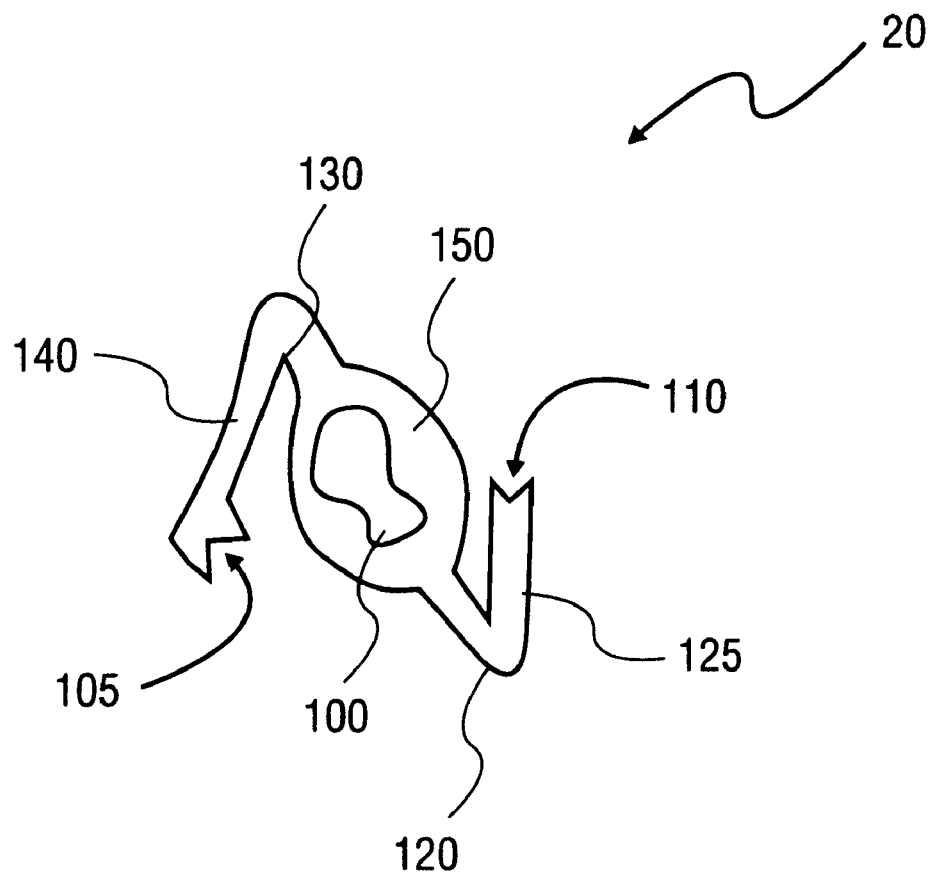
FIG. 6 is an isometric view of the member of FIG. 1 in accordance with one embodiment of the invention.

FIG. 6 shows an isometric view of member 20. Wall 150 forms aperture 100. First arm 140 and second arm 125 are shown to be at opposing angles. Therefore, first arm 140 may point in the proximal direction of housing 15 (not shown) and second arm 125 may point in the direction of the distal end of housing 15 (not shown). First angle 120 and second angle 130 of the first and second arm generally have an angle at approximately within 10° of each other but different angles may also be accommodated.

Distally-directed forces exerted on member 20 will cause an initial sliding movement of the entire assembly 10 (FIG. 1) without separating member 20 from housing 15. Continued exertion of a distally-directed axial force on member 20 after member 20 is locked in place with needle 45 will cause no further advancement of needle 45. Accordingly, the claimed invention offers an advantage over the prior art since the amount of force required to dislodge the device is so great that the device in its entirety would likely be destroyed.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A needle safety device comprising:
   a needle having a proximal and a distal end;
   a flexible member having a proximal end and a distal end and an aperture to receive the needle, the proximal end and the distal end having recessed regions to contact an outer surface of the needle; and
   a housing,
   wherein the proximal end and the distal end of the flexible member contact the housing at a first point located near the proximal end of housing and a second point located near the distal end of the housing.

2. The needle safety device of claim 1, further comprising:
   securing means for substantially preventing the flexible member from moving from a first longitudinal position to a second longitudinal position.

3. The needle safety device of claim 1, wherein the flexible member is angled at the first point at the proximal end approximately in the range of 20° to 90°.

4. The needle safety device of claim 1, wherein the flexible member is angled at the second point at the distal end approximately in the range of 20° to 90°.

5. The needle safety of claim 1, wherein the distal end of the flexible member contacts a portion of the housing at a distal end of the housing.

6. The needle safety device of claim 1, wherein the proximal end of the flexible member contacts a proximal end of the housing.

7. The needle safety device of claim 1, wherein the flexible member contacts the inner surface of the housing.

8. The needle safety device of claim 1, wherein the flexible member has a substantially Z-shape.

9. The needle safety device of claim 1, wherein the flexible member is slidably disposed over the needle.

10. A needle safety unit comprising:
    a needle;
    a housing for the needle, the housing having a proximal end and a distal end; and
    a member defining a hole to receive the needle, the member including a proximal arm and a distal arm with recessed regions to contact an outer surface of the needle,
    wherein the member contacts the housing at two opposing sides of an inner surface of the housing.

11. The needle safety unit of claim 10, wherein the member contacts the inner surface of the housing at opposing sides of the cover; and
    a first contact between the member and the housing located approximately at the distal end of the housing.

12. The needle safety unit of claim 11, wherein the member contacts the inner surface of the housing at the proximal end of the housing.

13. The needle safety unit of claim 10, wherein the member has a substantially Z-shape.

14. The needle safety unit of claim 10, further comprising:
    securing means for substantially preventing the member from advancing to the distal end of the cover.

15. The needle safety unit of claim 10, the member is capable of bending at an angle approximately in the range of 20° to 90°.

16. A needle safety device comprising:
    a needle;
    a member having an aperture to receive the needle, the member slidably disposed over the needle the member further having a proximal arm and a distal arm each with a recessed region to contact an outer surface of the needle; and
    securing means to secure the member to a housing that houses a portion of the needle wherein the member contacts the housing in at least two locations.

17. A method comprising:
    covering a needle with a housing;
    placing the needle through a flexible member within the housing such that an outer surface of the needle is in contact with a recessed region of each of a proximal and a distal arm of the flexible member; and
    contacting the flexible member at opposing sides of the housing.

18. The method of claim 17, wherein the flexible member forms at least one angle approximately in the range of 20° to 90°.

19. The method of claim 17, wherein the flexible member is slidably disposed over the needle.

20. The method of claim 17, wherein the flexible member has a substantially Z-shape.

* * * * *